(12) United States Patent
Reinhorn et al.

(10) Patent No.: US 6,671,398 B2
(45) Date of Patent: Dec. 30, 2003

(54) METHOD AND APPARATUS FOR INSPECTION OF PATTERNED SEMICONDUCTOR WAFERS

(75) Inventors: Silviu Reinhorn, Yavne (IL); Gilad Almogy, Yavne (IL)

(73) Assignee: Applied Materials, Inc., Santa Clara, CA (US)

(*) Notice: Subject to any disclaimer, the term of this patent is extended or adjusted under 35 U.S.C. 154(b) by 0 days.

(21) Appl. No.: 09/964,733

(22) Filed: Sep. 28, 2001

(65) Prior Publication Data
US 2002/0034325 A1 Mar. 21, 2002

Related U.S. Application Data

(63) Continuation of application No. 09/150,296, filed on Sep. 9, 1998, now Pat. No. 6,317,514.

(51) Int. Cl.[7] .................................................. G06K 9/00
(52) U.S. Cl. ................... 382/145; 382/149; 250/305; 250/397; 250/574
(58) Field of Search ......................... 382/144, 145, 382/149, 151, 203; 250/305, 306, 307, 309, 310, 227.29, 559.41, 559.18, 559.42, 574, 397; 348/126, 177; 356/237.2, 237.6, 369

(56) References Cited

U.S. PATENT DOCUMENTS

| | | | | |
|---|---|---|---|---|
| 4,286,293 A | * | 8/1981 | Jablonowski | 348/126 |
| 4,391,524 A | | 7/1983 | Steigmeier et al. | 356/445 |
| 4,441,124 A | * | 4/1984 | Heebner et al. | 348/126 |
| 4,562,356 A | | 12/1985 | Auth | 250/341.4 |
| 4,587,617 A | * | 5/1986 | Barker et al. | 382/149 |
| 4,820,927 A | | 4/1989 | Langner et al. | 250/492.24 |
| 4,849,645 A | * | 7/1989 | Mendenko et al. | 250/559.18 |
| 4,978,862 A | | 12/1990 | Silva, Deceased et al. | 250/562 |
| 4,988,877 A | | 1/1991 | Stokowksi et al. | |
| 5,146,509 A | * | 9/1992 | Hara et al. | 382/149 |
| 5,185,524 A | | 2/1993 | Page | 250/305 |

(List continued on next page.)

OTHER PUBLICATIONS

"Detecting Photoresist Residues Using Voltage Contrast ESCA" Hook; Physical Electronics Document No. 9801.

"Characterization of p–n Junctions and Surface–states on Silicon Devices by Photoemission Electron Microscopy"; M. Giesen et al.; Applied Physics, A64, pp. 423–430 (1997).

*Primary Examiner*—Jayanti K. Patel
*Assistant Examiner*—Sheela Chawan
(74) *Attorney, Agent, or Firm*—Sughrue Mion LLP.

(57) ABSTRACT

Novel method and apparatus are disclosed for inspecting a wafer surface to detect the presence thereon of exposed conductive material, particularly for determining the integrity of contact holes and vias, in semiconductor wafer manufacturing. The method comprises the steps of irradiating a spot of the wafer surface with a beam having a wavelength sufficiently shorter than the working function of the metal, such as deep UV light beam, collecting the electrons released by the irradiated wafer, generating an electrical signal that is a function of the collected electrons, and inspecting the signal to determine whether the contact holes or vias within the irradiated wafer spot are open. The apparatus comprises a vacuum chamber having therein a stage and chuck for supporting the wafer. An illumination source generates irradiating energy which is formed into a beam using appropriate optics so as to obtain the desired beam spot of the wafer's surface. an electron detector collects electrons released from the wafer surface and sends a corresponding signal to a processor for processing the signal to determine whether the metal at the bottom of the hole is exposed. Optionally, the light scattered by the wafer is detected by detectors arranged around the illuminating beam.

9 Claims, 3 Drawing Sheets

U.S. PATENT DOCUMENTS

| | | | | |
|---|---|---|---|---|
| 5,191,213 A | * | 3/1993 | Ahmed et al. | 250/310 |
| 5,286,974 A | | 2/1994 | Walker et al. | 250/305 |
| 5,302,830 A | | 4/1994 | Shivanandan | 250/342 |
| 5,442,242 A | | 8/1995 | Yoshida | 307/10.1 |
| 5,479,252 A | * | 12/1995 | Worster et al. | 356/237.5 |
| 5,502,306 A | | 3/1996 | Meisburger et al. | 250/310 |
| 5,563,411 A | * | 10/1996 | Kawata et al. | 250/306 |
| 5,602,899 A | | 2/1997 | Larson | 378/143 |
| 5,669,979 A | | 9/1997 | Elliott et al. | 134/1 |
| 5,699,447 A | | 12/1997 | Alumot et al. | 382/145 |
| 5,717,485 A | * | 2/1998 | Ito et al. | 356/237.1 |
| 5,828,067 A | | 10/1998 | Rushbrooke et al. | 250/370.11 |
| 5,930,588 A | | 7/1999 | Paniccia | 438/14 |
| 5,973,323 A | | 10/1999 | Adler et al. | 250/310 |
| 6,002,740 A | | 12/1999 | Cerrina et al. | 378/43 |
| 6,005,915 A | | 12/1999 | Hossain et al. | 378/70 |
| 6,087,659 A | | 7/2000 | Adler et al. | 250/310 |

* cited by examiner

METHOD AND APPARATUS FOR INSPECTION OF PATTERNED SEMICONDUCTOR WAFERS

This is a Continuation of application Ser. No. 09/150,296 filed Sep. 9, 1998 now U.S. Pat. No. 6,317,514, the disclosure of which is incorporated herein by reference.

FIELD OF THE INVENTION

This invention relates to method and apparatus for the inspection of patterned semiconductor wafers and particularly for the detection of defects that may exist in the upper layer of a wafer which comprises structures having a high aspect ratio, such as high aspect ratio contact holes and vias, and structures that may have residual metal defects.

BACKGROUND OF THE INVENTION

The art comprises methods for detecting possible defects in patterned wafers. A summary of the state of the art concerning such detection is included in U.S. Pat. No. 5,699,447, and is incorporated herein by reference. In said patent, an inspection apparatus is described which comprises a table for receiving a wafer to be inspected, a source of a laser beam, which beam scans the surface of the wafer, and a plurality of light collectors for collecting the light scattered from the wafer and transmitting the scattered light to a plurality of detectors. The output of the detectors is fed to a processor, which produces information indicating locations on the wafer in which the presence of a defect is suspected.

With optical scanning, it is possible to detect defects that are on top of the upper layer of the inspected wafer, or under transparent layers. As design rules progress, higher importance is given to detecting smaller defects. The general approach in the industry is to increase the imaging resolution by, for example, reducing the wavelength of the light source or replacing light with other radiation source.

However, when the upper scanned layer is comprised of high aspect ratio (HAR) structures, the defect detection becomes problematic. A typical defect that is difficult to detect, if impossible, is illustrated in FIG. 1. Numerals 10, 11 and 12 indicate respectively the metal layer, the dielectric layer, and the contact holes or "vias" in layer 11. The vias are formed in the etch process. When a contact hole or via 12 is filled with another metal to form the electrical connection between two metal layers, this connection should be well closed mechanically and electrically. In FIG. 1 it is seen that, after the etch process two contact or vias are completely obstructed or closed by non-conductive matter 13 and 14, and another via is partially obstructed or closed by non-conductive matter 15. The non-conductive matter may be polymer or residue dielectric material that has not been successfully etched (removed) or particles that have deposited on the wafer in the course of its processing. Such defects are called partially opened contacts/vias. Moreover, sometimes it happens that the process failed to create the contact holes entirely, e.g.,. due to problems with the mask or the stepper. Such a defect is called a "missing" contact hole.

Defects, such as partials (partially opened contacts/vias) and missing contact holes are crucial for the final yield of the FAB, because such defects are generally "killer" defects, I.e., they make the dies inoperative. With the current technologies of optical scanning, it is difficult to detect defects on the bottom of the vias or contacts, because of the following reason. The aspect ratio of contacts and vias, viz. the ratio of their height to their diameter, with today's technology is in the order of 5:1 to 10:1. The vias or contact diameter is about 0.25 microns and is going to decrease with the development of the technology. The wavelength of the light used for inspection illumination with today's technology is about 0.5 microns. Under such conditions, the light cannot reach the bottom of the vias or contacts, and thus, the defects there are not seen. The main reason is that the structure of the hole, having a higher dielectric constant insulator surrounding a HAR hole of low (i.e., air) dielectric constant acts as an "anti-waveguide" to repel the light from the contact hole. This phenomenon behaves much the same as a leaky mode in a waveguide.

There is, therefore, a need for a means that will permit the detection of defects not revealed by optical scanning according to the present art, and, in particular, the detection of the total or partial obstruction of contact holes by non-conductive matter.

Other defects of interest for the present invention are, for example, residual metal defects. These defects are of particular interest since they can short out the circuit. Such defects can show up especially in metal deposition and demacene processes, depicted in FIGS. 1B and 1C respectively. In FIG. 1B, a metal layer is deposited upon the insulator layer 100. Then, trenches (or other structures) 130 are etched, thereby leaving only metal structures 110 upon the insulator 100. However, it may occur that some metal residue 140 remains inside the trenches, and may cause a short. In FIG. 1C, trenches (or other structures) are first formed in insulator layer 105. Then, the trenches are filled with metal (generally tantalum or copper) and the entire structure is polished to remove any excess metal from the top surface of the insulator 105, thereby forming conductive structures 115 (such as bit lines). However, some scratches may form on the top surface of the insulator and be filled with the metal thereby creating a metal residue defect 125, which can potentially short the circuit. Thus, it is important to detect the presence of such metal residue defects.

Another technology of interest for the present invention relates to charged particle energy analyzer. Specifically, a specimen is placed in the analyzer, and is bombarded with ionizing radiation so as to dislodge charged particles from the specimen's surface. The particles are then collected, and their energy spectrum is used to determine the chemical constitution of the surface of the specimen. With respect to this technology, the reader may refer to U.S. Pat. Nos. 5,185,524 and 5,286,974.

A well known technique to release charged particles, i.e., electrons from a material's surface is by illumination of the surface. This field is sometimes referred to a photo emission electron microscopy (PEEM) and has previously been used to observe samples. For an example of a PEEM for use with biological samples the reader is referred to U.S. Pat. No. 5,563,411 to Kawata et al. For use of PEEM in analysis of semiconductor structure the reader is referred to "Characterization of p-n Junctions and Surface_states on Silicon Devices by Photoemission Electron Microscopy" M.Giesen et al., Appl. Phys. A 64, 432–430, 1997.

More relevant to the present invention is the following discussion of the physics behind photo-emission. When the energy of a photon $E=hc/\lambda$ that impinges on the material is larger than its working function, i.e. $\phi<hc/\lambda$, there is a probability P that an electron will be released from the surface. Here, E is the kinetic energy of a photon, h is the Plank constant, and c is the speed of light.

The working function of any material represents the amount of energy that one should apply in order to release an electron from the material surface. Usually, the working functions of metals are much lower than those of insulators, because the amount of free electrons in metals is larger than in insulators. The working functions of some commonly used metals in the semiconductor industry and their corresponding wavelengths are summarized in the table below.

| Metal | $\phi$(eV) | Wavelength (nm) |
|-------|------------|-----------------|
| Al    | 4.28       | 289             |
| Cu    | 4.65       | 266             |
| Ti    | 4.33       | 285             |
| W     | 4.55       | 270             |

As can be seen from the table, a wavelength of less than 266 nm, e.g., deep UV illumination, is required in order to release electrons from these metals.

Another technology of interest for the present invention relates to inspection of specimen using x-rays. Generally, an electron beam is caused to impinge upon a metal, such as aluminum, to generate x-rays.

The emitted x-ray is formed into a beam and caused to impinge upon the specimen, thus causing emission of photoelectrons. The photoelectrons are collected and an analyzer is used to determine the chemical species on the surface of the specimen. Such technology is described, for example, in U.S. Pat. Nos. 5,444,242 and 5,602,899 both to Larson and both assigned to Physical Electronics, Inc. Physical Electronics' marketing literature (see Physical Electronics document No. 9801 authored by Dan Hook) describes the use of such technology for inspecting wafers to determine the presence of photoresist residue. However, as can be understood from the cited patents and literature, such system is cumbersome and may not be readily implemented for "in-line" inspection of wafers, especially as far as tilting the wafers is concerned. Also, the throughput is limited due to the relatively low intensity of the X-ray beam that is produced with the aid of an energetic electron beam that impinge upon an Aluminum specimen.

SUMMARY OF THE INVENTION

The present invention provides for a method and apparatus for inspecting HAR contact holes and vias.

The method of the invention is also advantageously applicable to the detection of non-conductive or conductive foreign matter at any location on the wafer.

It is a purpose of the invention to provide a method and an apparatus that are quickly operable and provide high throughput.

It is another purpose to provide a method and an apparatus that are compatible, and even combinable, with optical inspection methods.

Other purposes and advantages of the invention will appear as the description proceeds.

The solution, provided by the invention, to the problem of the detection of the total or partial obstruction of contact holes by non-conductive matter, is based on the idea of material classification rather than conventional imaging or scattered light detection. Basically, therefore, the method of the invention comprises the step of verifying the type of material at any location on the wafer, and particularly at the bottom of the vias or contacts. This same method can also be advantageously used to detect other defects, such as metal residue defects.

Normally, at the bottom of a via or contact, there is metal, and the surrounding is an insulator. One of the physical parameters that distinguishes metals from insulators is their working function ($\phi$). The method of the invention, therefore, comprises, in its preferred form, the step of determining whether the material at the bottom of the vias or contacts is a metal or an insulator by distinguishing between them according to their working function.

The method according to the invention, comprises irradiating a spot of the wafer surface with a beam having a wavelength sufficiently shorter than the working function of the metal, such as deep UV beam, collecting the electrons released by the irradiated wafer, generating an electrical signal that is a function of the collected electrons, and inspecting the signal to determine whether any non-conductive material is present on said spot of the wafer, and particularly, if said spot comprises contact holes or vias, whether the contact holes or vias within the irradiated wafer spot are open. The decision may be reached by comparing the electrical signals measured in adjacent dies, or, if the dies have a periodic structure, by comparing the signals obtained from adjacent cells within the die.

The invention also provides an apparatus for carrying out the method of the invention. The apparatus comprises a vacuum chamber having therein a stage and chuck for supporting the wafer. An illumination source generates irradiating energy which is formed into a beam using appropriate optics so as to obtain the desired beam spot of the wafers surface. An electron detector collects electrons released from the wafer surface and sends a corresponding signal to a processor for processing the signal to determine whether the metal in said beam spot, and particularly at the bottom of any hole within said spot, is exposed.

Preferably the electron detector comprises at least one electrode mounted above the wafer and having a positive potential with respect to the wafer.

The invention further provides for novel apparatus—hereinafter called, "hybrid optical photo-electron wafer inspection apparatus", or, briefly, "hybrid apparatus"—which enables concurrent optical inspection of the wafer and electron detection for HAR opening verification.

BRIEF DESCRIPTION OF THE DRAWING

The various advantages and features of the invention can be better understood from the detailed description provided below, wherein a reference is made to the accompanying drawings, in which.

DETAILED DESCRIPTION OF THE PREFERRED EMBODIMENTS

The preferred embodiments hereinafter described relate to the determination of whether a high aspect ratio contact hole or via is open. However, as hereinbefore stated, the invention is not limited to such embodiments or in general to the determination of the presence of non-conductive matter in holes or vias, but includes its determination at any location on the wafer. In the embodiments hereinafter described by way of illustration the wafer is irradiated with light of short wavelength to cause release of electrons from the wafer. The electrons are collected to generate a signal, and the signal is analyzed to determine whether the contact holes or vias are open.

While the preferred embodiments described herein refer to a DUV laser light, it should be appreciated that other short wavelength light sources can be used. Specifically, laser light has been generally preferred for scanning (e.g., laser printers, CD players, etc.) because its spatial coherence permits creating a small beam spot on the substrate. Notably, if one uses a spatially incoherent beam from a source other than a laser, it is hard to obtain a small and intense beam spot. However, since the beam spot diameter is proportional to the wavelength, according to the invention, one can choose an incoherent beam having sufficiently short wavelength and obtain a desired beam diameter.

Thus, the invention will be described hereinafter with reference to the use of a deep UV light beam, but this is not to be construed as a limitation, and it should be understood that what is said with reference to the illumination of a spot of the wafer surface with a deep UV light beam, equally applies to the irradiation of said spot with other light sources.

The illumination or irradiation of the wafer surface and the collection of the released electrons should be carried out under a vacuum.

Figure 2:
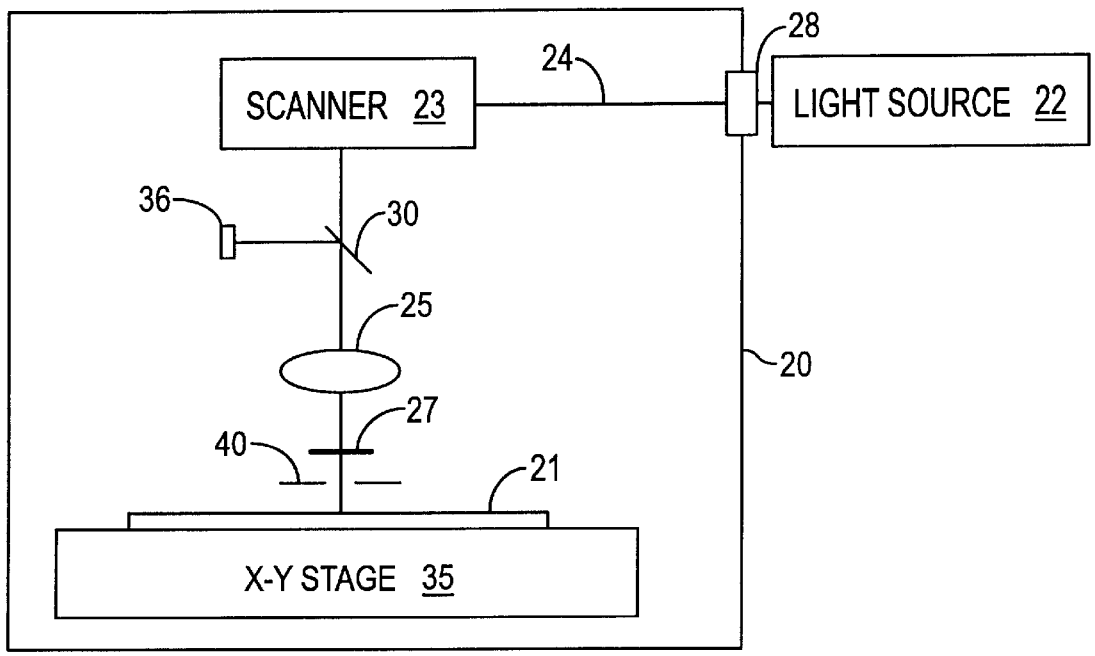
FIG. 2 schematically illustrates an apparatus according to an embodiment of the invention.

In FIG. 2, numeral 20 generally designates a vacuum chamber and 21 is the wafer under inspection. An X-Y stage 35 is provided for supporting the wafer 21 in chamber 20, although it should be appreciated that other stages, such as a turntable, can be used for scanning the wafer. Alternatively, the stage can be stationary and the optical head can be scanned over the entire wafer.

Element 22 is a short wavelength light source and 23 indicates a scanner for shifting the light beam 24 to scan the wafer strip-wise. The light beam 24 is focused by objective 25 to form a spot on the wafer surface. Vacuum chamber 20 also contains an electron detector shown at 27, which has an opening for the passage of the light beam issuing from objective 25. Numeral 40 schematically indicates an optional biased electrode.

As shown in FIG. 2, it is preferable to have the light source 22 outside the vacuum chamber 20, and to allow the beam 24 to enter the chamber via window 28. Then the beam can be made to impinge upon the scanner 23. Alternatively, the scanner may also be situated outside the vacuum chamber 20, and the scanned beam can be made to enter the chamber 20 via a window.

In operation, the beam is made to scan the wafer covering strips having a width determined by the scanning angle of the scanner 23 and length determined by the travel of the stage in a first direction, say in the Y direction. Once the beam completes scanning one strip, the stage moves in the second direction, say the X direction, an amount somewhat smaller than the strip's width, to start scanning a second strip. The motion in the X direction is made smaller than the width of the strip to allow for some overlap. Of course, if a turntable is provided, the scanning would be in the r-theta coordinates.

As the light beam impinges upon metal at the bottom of a contact hole or via, electrons are emitted and detected by the detector 27. On the other hand, if the contact hole or via is fully blocked, the energy of the impinging light beam would be insufficient to cause electron emission, SO that an alarm can be issued that the contact hole is blocked or missing. Similarly, when the contact hole is partially blocked fewer electrons will be emitted, and a corresponding signal would be provided by the detector 27 so that an alarm may be issued. The investigation of the signal can be done using methods such as a threshold, or any suitable algorithm for die-to-die, or a cell-to-cell comparisons, etc.

In a similar manner, when inspecting the substrate for metal residue or similar defects, the wafer can be scanned to locate electron emission from areas where there should be only an insulator. For example, when the scan is performed in the trenches 130 of FIG. 1B or on the insulator part 105 of FIG. 1C, no electrons should be emitted. If electrons are emitted, it signals that there's metal residue inside on an insulating layer and a defect alarm should be issued.

The illumination or irradiated spot may have an area that contains a number of contact/vias at a time, and therefore the detected photo electrons, as well as the scattered light, may belong to all of them. Therefore, as provided by the Nyquist theorem, when a defect is detected, its location is known with an accuracy that is limited by the sampling rate of the detector's signal sampling. In the preferred embodiment, the sampling rate can be adjust so that the defect can be traced to nearly one of several holes which are within the field of view of a review tool. That is, according to the preferred embodiment, there is no need to have a high sampling rate so as to detect the exact location of the plugged or obstructed hole. Instead, the sampling rate is chosen so that the plugged hole can be identified as one of several holes which would appear in a field of view of the review tool, since when such a defect is detected the wafer will be moved to a review tool for further investigation. Therefore, all that needed is to identify for the review tool a general location'so that the exact location can be found within the field of view.

FIG. 2 also shows an optional biased electrode 40 which provides two advantages. First, by biasing the electrode with respect to the wafer, it helps pull the electrons from the bottom of the contact holes. Specifically, since the invention is aimed at HAR holes, electrons emitted from the bottom of the hole may hit the walls of the hole and, therefore, not exit the hole. By applying a field over the wafer, the electrons will be attracted vertically and exit the hole easily. Second, in order to achieve a high throughput, it is important to use high speed scanning. Consequently, it is necessary to collect the electrons quickly. By applying the field over the wafer, the emitted electrons are caused to accelerate towards the detector, thereby shortening the time it takes to collect the electrons. Also, it is important to keep the wafer (specimen) neutral during the inspection process. This can be done by ground connecting the wafer through the chuck.

In some cases, the conductivity of the wafer might be poor. Consequently, when the electrons are pulled from the wafer, a positive potential may be left on the wafer. This phenomenon is known in the art as "charging effect." In order to avoid this charging effect, an electron gun numbered (not shown) is optionally placed in the vacuum chamber in order to direct electrons to areas that are already scanned in order to keep the wafer neutral.

Figure 3:
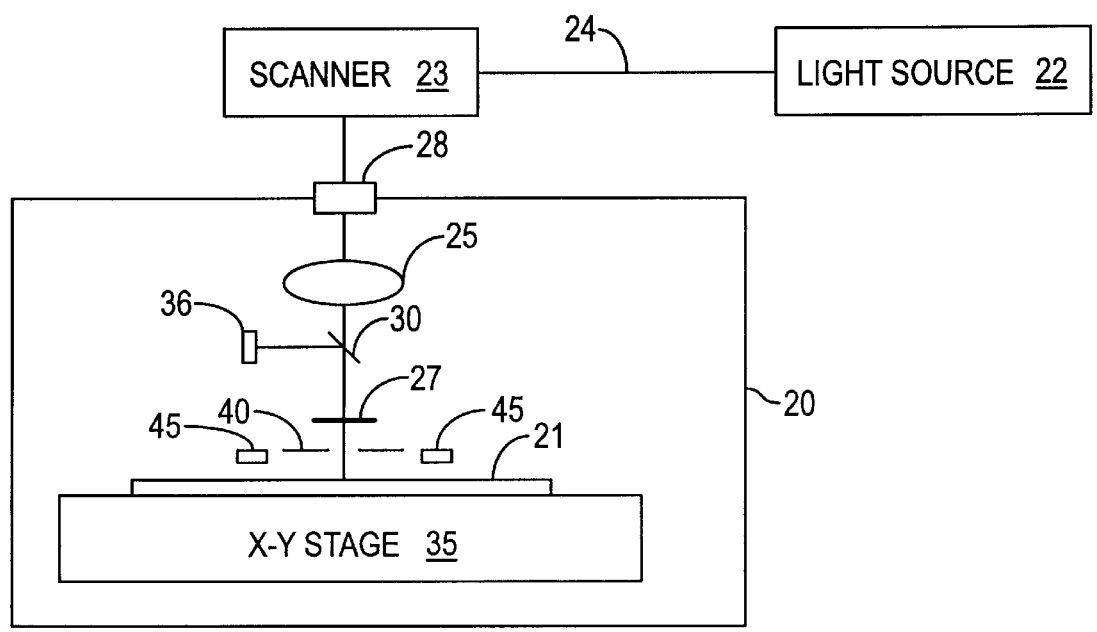
FIG. 3 schematically illustrates an apparatus according to another embodiment of the invention.

A hybrid defect inspection/HAR inspection system is depicted in FIG. 3. Much of the elements depicted in FIG. 3 are similar to those shown in FIG. 2 and, therefore, these elements are identified with the same numerals. The system of FIG. 3 takes advantage of the fact that, while usually sources of shorter wavelength light produce smaller intensity, scattering of the light beam by defects is increased as a function of $1/\lambda^n$, where $\lambda$ is the illumination wavelength. Therefore, the system of FIG. 3 uses scattering of the light for defect detection. For that purpose, preferably four detectors, (only two detectors are shown, indicated as elements 45) are arranged around the beam so as to detect any light scattered from the wafer. Such an arrangement is generally known as dark field arrangement, as used, for example, in the WF 736 inspection systems available from Applied Materials of Santa Clara, Calif., and described in the above-cited U.S. Pat. No. 5,699,447.

An optional feature which can be implemented in either systems of FIGS. 2 and 3 is exemplified in FIG. 2. Specifically, a "bright field" detector 36 can be added in addition to the dark field detector. In FIG. 2, a dichroic mirror 30 is used to deflect the bright field reflection light towards the bright field detector 36. Of courses other optics can be used to direct the reflected light towards the bright field detector.

As can be understood, the invention as exemplified by the preferred embodiment of FIG. 3 is advantageous in that it enables simultaneous optical inspection of the wafer for defect and electron detection for inspection of HAR contact holes and vias. That is, when the beam 24 impinges upon the wafer the electron sensor 27 can be used to detect any electrons emitted from the wafer—thereby indicating that a contact hole is unobstructed—and the light detectors can be used to detect any scattered light—thereby indicating a defect on the wafer's surface (as is known in dark field wafer inspection).

Figure 1A:
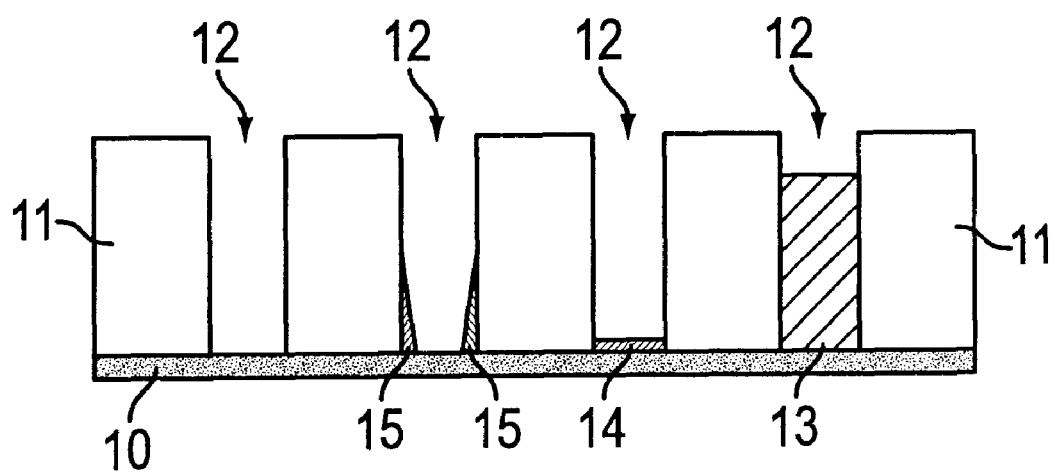
FIG. 1A schematically illustrates opened and closed contact holes in a wafer.
Figure 1B:
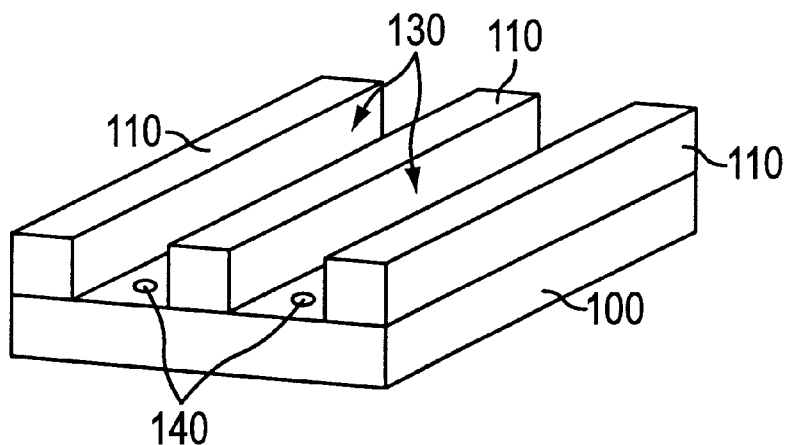
FIG. 1B schematically illustrates residual metal defects occurring in the metal deposition process.
Figure 1C:
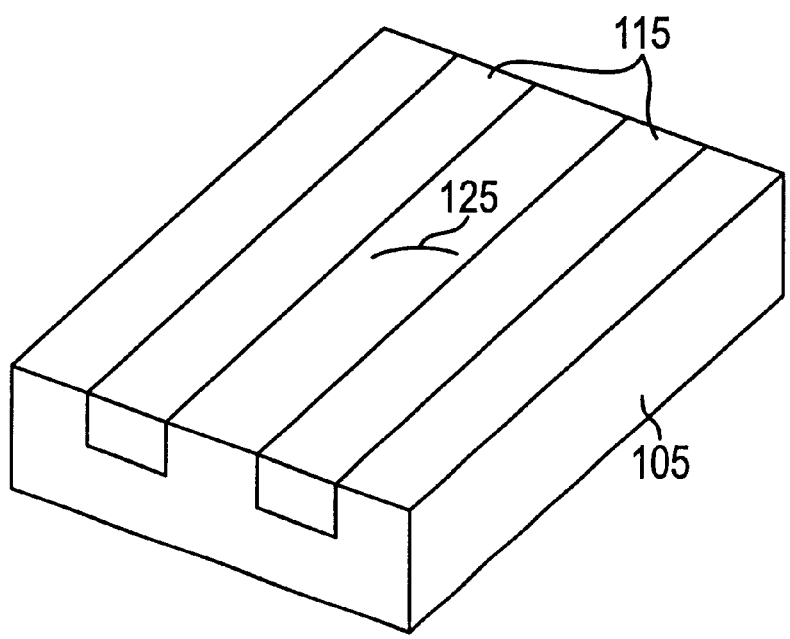
FIG. 1C schematically illustrates residual metal defects occurring in the damacene process.

Another advantage of the hybrid system of FIG. 3 is that it enables "on-the-fly" classification of certain metal defects. That is, when a metal defect, such as the metal residue defects shown in FIGS. 1B and 1C, are present, the light scattering system will sense the defect and provide an alarm, while the electron collection system will enable indication of whether the defect is made of metal. This can help in distinguishing between washing stains, "empty" scratches, metal residue, etc., thereby assisting in the classification of the detected defects.

While specific embodiments of the invention have been described for the purpose of illustration, it will be understood that the invention may be carried into practice by skilled persons with many modifications, variations and adaptations, without departing from its spirit or exceeding the scope of the claims.

What is claimed is:

1. A hybrid method of inspecting a patterned semiconductor wafer, comprising the steps of:
   (a) generating an illumination beam;
   (b) impinging said illumination beam upon said wafer surface;
   (c) performing material classification inspection of said wafer surface using electrons released therefrom, the material classification inspection comprising the steps of:
      (c1) collecting the electrons emitted from said wafer surface due to the impingement of said beam;
      (c2) generating a classification signal corresponding to the amount of electrons collected from the wafer in step (c1);
      (c3) analyzing the classification signal generated in step (c2) to determine the presence of defects on the wafer based on the material classification; and
   (d) performing scattered light detection of the illumination beam reflected from said wafer surface, the scattered light detection comprising the steps of:
      (d1) receiving light scattered from said wafer surface onto a plurality of detectors; and
      (d2) determining an existence of surface defects based on the light received by said plurality of detectors in step (d1).

2. The hybrid method of inspecting said patterned semiconductor wafer according to claim 1, wherein the illuminating beam is impinged on a high aspect ratio wafer surface.

3. The hybrid method of inspecting said patterned semiconductor wafer according to claim 1, wherein the step of receiving light scattered from said wafer surface is performed using a dark field arrangement.

4. The hybrid method of inspecting said patterned semiconductor wafer according to claim 3, further comprising the step of performing scattered light detection using a bright field detector.

5. The hybrid method of inspecting said patterned semiconductor wafer according to claim 1, wherein the step of generating an illumination beam comprises generating a deep UV light beam.

6. The hybrid method of inspecting said patterned semiconductor wafer according to claim 1, wherein the material classification analyzing step comprises comparing the classification signal to a reference signal chosen from among a database signal and a corresponding signal produced from adjacent die or cell.

7. The hybrid method of inspecting said patterned semiconductor wafer according to claim 1, wherein the material classification analyzing step comprises using the classification signal to determine a working function of the inspected material on the wafer surface.

8. The hybrid method of inspecting said patterned semiconductor wafer according to claim 1, wherein the scattered light detection and the material classification inspection are performed simultaneously.

9. The hybrid method of inspecting said patterned semiconductor wafer according to claim 1, further comprising the steps of first using the scattered light detection to sense a surface defect and subsequently using the material classification inspection to classify a type of material corresponding to the surface defect.

* * * * *